United States Patent
Brown

(10) Patent No.: US 8,015,033 B2
(45) Date of Patent: *Sep. 6, 2011

(54) TREATMENT REGIMEN COMPLIANCE AND EFFICACY WITH FEEDBACK

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 194 days.

This patent is subject to a terminal disclaimer.

(21) Appl. No.: 11/845,317

(22) Filed: Aug. 27, 2007

(65) Prior Publication Data
US 2008/0200771 A1    Aug. 21, 2008

Related U.S. Application Data

(63) Continuation of application No. 10/233,296, filed on Aug. 30, 2002, which is a continuation-in-part of application No. 09/304,477, filed on May 3, 1999, now abandoned, and a continuation-in-part of application No. 09/237,194, filed on Jan. 26, 1999, which is a continuation of application No. 08/481,925, filed on Jun. 7, 1995, now Pat. No. 5,899,855, which is a continuation of application No. 08/233,397, filed on Apr. 26, 1994, now abandoned.

(51) Int. Cl.
  *G06Q 50/00* (2006.01)
  *G06Q 10/00* (2006.01)
(52) U.S. Cl. ............................................. 705/3; 705/2
(58) Field of Classification Search ........................ 705/3
    See application file for complete search history.

(56) References Cited

U.S. PATENT DOCUMENTS

| | | | |
|---|---|---|---|
| 4,051,522 | A | 9/1977 | Healy et al. |
| 4,130,881 | A | 12/1978 | Haessler et al. |
| 4,151,407 | A | 4/1979 | McBride et al. |
| 4,253,521 | A | 3/1981 | Savage |
| 4,347,568 | A | 8/1982 | Giguere et al. |
| 4,347,851 | A | 9/1982 | Jundanian |
| 4,360,345 | A | 11/1982 | Hon |
| 4,546,436 | A | 10/1985 | Schneider et al. |
| 4,576,578 | A | 3/1986 | Parker et al. |
| 4,729,381 | A | 3/1988 | Harada et al. |

(Continued)

FOREIGN PATENT DOCUMENTS
EP    0286456    10/1988
(Continued)

OTHER PUBLICATIONS
1995_10_30_Mortorala_introduces_PCMCIA28.8_Modem.
(Continued)

*Primary Examiner* — Gerald J. O'Connor
*Assistant Examiner* — Sheetal R Rangrej
(74) *Attorney, Agent, or Firm* — Christopher P. Maiorana, PC

(57) ABSTRACT

A method and system for interaction with a community of individuals, relating to compliance with and effectiveness of treatment regimens, including supply and use of pharmaceuticals, using a protocol or other intelligent message which acts in place of a service provider and which is capable of collecting or imparting information to patients in place thereof. Individuals interact with the protocol or intelligent message to provide assistance in all aspects of treatment regimen compliance, data collection, supply or delivery, review and modification.

20 Claims, 3 Drawing Sheets

U.S. PATENT DOCUMENTS

| | | | |
|---|---|---|---|
| 4,731,726 A * | 3/1988 | Allen, III | 600/300 |
| 4,768,229 A | 8/1988 | Benjamin et al. | |
| 4,779,199 A | 10/1988 | Yoneda et al. | |
| 4,796,639 A | 1/1989 | Snow et al. | |
| 4,799,199 A | 1/1989 | Scales, III et al. | |
| 4,803,625 A | 2/1989 | Fu et al. | |
| 4,838,275 A | 6/1989 | Lee | |
| 4,858,354 A | 8/1989 | Gettler | |
| 4,858,617 A | 8/1989 | Sanders | |
| 4,897,869 A | 1/1990 | Takahashi | |
| 4,899,839 A | 2/1990 | Dessertine et al. | |
| 4,907,973 A | 3/1990 | Hon | |
| 4,933,873 A | 6/1990 | Kaufman et al. | |
| 4,950,246 A * | 8/1990 | Muller | 604/154 |
| 5,007,429 A | 4/1991 | Treatch et al. | |
| 5,016,172 A | 5/1991 | Dessertine | |
| 5,019,974 A * | 5/1991 | Beckers | 600/316 |
| 5,024,225 A | 6/1991 | Fang | |
| 5,025,374 A | 6/1991 | Roizen et al. | |
| 5,034,807 A | 7/1991 | Von Kohorn | |
| 5,056,059 A | 10/1991 | Tivig et al. | |
| 5,065,315 A | 11/1991 | Garcia | |
| 5,068,536 A | 11/1991 | Rosenthal | |
| 5,077,476 A | 12/1991 | Rosenthal | |
| 5,095,798 A | 3/1992 | Okada et al. | |
| 5,109,974 A | 5/1992 | Beer et al. | |
| 5,111,817 A | 5/1992 | Clark et al. | |
| 5,120,230 A | 6/1992 | Clark et al. | |
| 5,128,752 A | 7/1992 | Von Kohorn | |
| 5,134,391 A | 7/1992 | Okada | |
| 5,142,358 A | 8/1992 | Jason | |
| 5,142,484 A | 8/1992 | Kaufman et al. | |
| 5,176,502 A | 1/1993 | Sanderson et al. | |
| 5,182,707 A | 1/1993 | Cooper et al. | |
| 5,204,670 A | 4/1993 | Stinton | |
| 5,222,020 A | 6/1993 | Takeda | |
| 5,227,874 A | 7/1993 | Von Kohorn | |
| 5,249,044 A | 9/1993 | Von Kohorn | |
| 5,261,401 A | 11/1993 | Baker et al. | |
| 5,262,943 A | 11/1993 | Thibado et al. | |
| 5,299,121 A | 3/1994 | Brill et al. | |
| 5,307,263 A | 4/1994 | Brown | |
| 5,329,459 A | 7/1994 | Kaufman et al. | |
| 5,329,608 A | 7/1994 | Bocchieri et al. | |
| 5,331,549 A | 7/1994 | Crawford, Jr. | |
| 5,339,821 A | 8/1994 | Fujimoto | |
| 5,341,291 A | 8/1994 | Roizen et al. | |
| 5,344,324 A | 9/1994 | O'Donnell et al. | |
| 5,357,427 A | 10/1994 | Langen et al. | |
| 5,366,896 A | 11/1994 | Margrey et al. | |
| 5,381,138 A | 1/1995 | Stair et al. | |
| 5,390,238 A | 2/1995 | Kirk et al. | |
| 5,399,821 A | 3/1995 | Inagaki et al. | |
| 5,410,471 A | 4/1995 | Alyfuku et al. | |
| 5,434,611 A | 7/1995 | Tamura | |
| 5,441,047 A | 8/1995 | David et al. | |
| 5,454,721 A | 10/1995 | Kuch | |
| 5,454,722 A | 10/1995 | Holland et al. | |
| 5,467,269 A | 11/1995 | Flaten | |
| 5,471,039 A | 11/1995 | Irwin, Jr. et al. | |
| 5,483,276 A | 1/1996 | Brooks et al. | |
| 5,488,423 A | 1/1996 | Walkingshaw et al. | |
| 5,501,231 A | 3/1996 | Kaish | |
| 5,502,636 A | 3/1996 | Clarke | |
| 5,504,519 A | 4/1996 | Remillard | |
| 5,515,303 A * | 5/1996 | Cargin et al. | 361/679.32 |
| 5,517,405 A | 5/1996 | McAndrew et al. | |
| 5,542,420 A | 8/1996 | Goldman et al. | |
| 5,544,649 A | 8/1996 | David et al. | |
| 5,549,117 A | 8/1996 | Tacklind et al. | |
| 5,550,575 A | 8/1996 | West et al. | |
| 5,553,609 A | 9/1996 | Chen et al. | |
| 5,558,638 A | 9/1996 | Evers et al. | |
| 5,569,212 A | 10/1996 | Brown | |
| 5,572,421 A * | 11/1996 | Altman et al. | 705/3 |
| 5,574,828 A | 11/1996 | Hayward et al. | |
| 5,576,952 A | 11/1996 | Stutman et al. | |
| 5,583,758 A | 12/1996 | McIlroy et al. | |
| 5,594,637 A | 1/1997 | Eisenberg et al. | |
| 5,596,994 A | 1/1997 | Bro | |
| 5,597,307 A | 1/1997 | Redford et al. | |
| 5,601,435 A | 2/1997 | Quy | |
| 5,619,991 A | 4/1997 | Sloane | |
| 5,624,265 A | 4/1997 | Redford et al. | |
| 5,628,309 A | 5/1997 | Brown | |
| 5,631,844 A | 5/1997 | Margrey et al. | |
| 5,633,910 A | 5/1997 | Cohen | |
| 5,642,731 A | 7/1997 | Kehr | |
| 5,642,936 A | 7/1997 | Evans | |
| 5,664,228 A | 9/1997 | Mital | |
| 5,670,711 A | 9/1997 | Detournay et al. | |
| 5,675,635 A | 10/1997 | Vos et al. | |
| 5,678,562 A | 10/1997 | Sellers | |
| 5,680,590 A | 10/1997 | Parti | |
| 5,687,322 A | 11/1997 | Deaton et al. | |
| 5,687,717 A | 11/1997 | Halpern et al. | |
| 5,704,366 A | 1/1998 | Tacklind et al. | |
| 5,704,902 A | 1/1998 | Vandenbelt et al. | |
| 5,711,297 A | 1/1998 | Iliff | |
| 5,715,451 A | 2/1998 | Marlin | |
| 5,717,913 A | 2/1998 | Driscoll | |
| 5,720,733 A | 2/1998 | Brown | |
| 5,722,418 A | 3/1998 | Bro | |
| 5,727,153 A | 3/1998 | Powell | |
| 5,732,709 A | 3/1998 | Tacklind et al. | |
| 5,752,234 A | 5/1998 | Withers | |
| 5,760,771 A | 6/1998 | Blonder et al. | |
| 5,772,585 A | 6/1998 | Lavin et al. | |
| 5,782,814 A | 7/1998 | Brown et al. | |
| 5,785,650 A | 7/1998 | Akasaka et al. | |
| 5,791,342 A | 8/1998 | Woodard | |
| 5,792,117 A | 8/1998 | Brown | |
| 5,793,969 A | 8/1998 | Kamentsky et al. | |
| 5,796,393 A | 8/1998 | MacNaughton | |
| 5,802,494 A | 9/1998 | Kuno | |
| 5,810,747 A | 9/1998 | Brudny et al. | |
| 5,819,735 A | 10/1998 | Mansfield et al. | |
| 5,822,544 A | 10/1998 | Chaco et al. | |
| 5,825,283 A | 10/1998 | Camhi | |
| 5,827,180 A | 10/1998 | Goodman | |
| 5,828,943 A | 10/1998 | Brown | |
| 5,835,896 A | 11/1998 | Fisher et al. | |
| 5,836,304 A * | 11/1998 | Kellinger et al. | 600/300 |
| 5,842,976 A | 12/1998 | Williamson | |
| 5,868,669 A | 2/1999 | Iliff | |
| 5,875,432 A | 2/1999 | Sehr | |
| 5,879,163 A | 3/1999 | Brown et al. | |
| 5,893,077 A | 4/1999 | Griffin | |
| 5,893,098 A | 4/1999 | Peters et al. | |
| 5,897,493 A | 4/1999 | Brown | |
| 5,899,855 A | 5/1999 | Brown | |
| 5,911,687 A | 6/1999 | Sato et al. | |
| 5,913,310 A | 6/1999 | Brown | |
| 5,918,603 A | 7/1999 | Brown | |
| 5,920,477 A | 7/1999 | Hofberg et al. | |
| 5,933,136 A | 8/1999 | Brown | |
| 5,935,060 A | 8/1999 | Iliff | |
| 5,950,632 A * | 9/1999 | Reber et al. | 128/898 |
| 5,960,403 A | 9/1999 | Brown | |
| 5,961,446 A | 10/1999 | Beller et al. | |
| 5,983,217 A | 11/1999 | Khosravi-Sichani et al. | |
| 5,987,471 A | 11/1999 | Bodine et al. | |
| 5,995,969 A | 11/1999 | Lee et al. | |
| 5,997,476 A | 12/1999 | Brown | |
| 6,001,065 A | 12/1999 | DeVito | |
| 6,022,315 A | 2/2000 | Iliff | |
| 6,022,615 A | 2/2000 | Rettenbacher | |
| 6,029,138 A | 2/2000 | Khorasani et al. | |
| 6,046,761 A | 4/2000 | Echerer | |
| 6,049,794 A | 4/2000 | Jacobs et al. | |
| 6,050,940 A | 4/2000 | Braun et al. | |
| 6,055,314 A | 4/2000 | Spies et al. | |
| 6,055,487 A | 4/2000 | Margery et al. | |
| 6,055,506 A | 4/2000 | Frasca, Jr. | |
| 6,057,758 A | 5/2000 | Dempsey et al. | |
| 6,110,148 A | 8/2000 | Brown et al. | |
| 6,138,145 A | 10/2000 | Kawanaka | |

| | | | |
|---|---|---|---|
| 6,151,581 A * | 11/2000 | Kraftson et al. | 705/3 |
| 6,151,586 A | 11/2000 | Brown | |
| 6,161,095 A | 12/2000 | Brown | |
| 6,168,563 B1 | 1/2001 | Brown | |
| 6,177,940 B1 | 1/2001 | Bond et al. | |
| 6,189,029 B1 | 2/2001 | Fuerst | |
| 6,248,065 B1 | 6/2001 | Brown | |
| 6,270,456 B1 | 8/2001 | Iliff | |

FOREIGN PATENT DOCUMENTS

| | | |
|---|---|---|
| EP | 0320749 | 6/1989 |
| EP | 370599 | 5/1990 |
| EP | 0461910 | 12/1991 |
| EP | 508912 | 10/1992 |
| EP | 526166 | 2/1993 |
| EP | 0558975 | 9/1993 |
| EP | 0653718 | 5/1995 |
| EP | 676709 | 10/1995 |
| EP | 680727 | 11/1995 |
| EP | 761160 | 3/1997 |
| EP | 08131551 | 12/1997 |
| EP | 0251520 | 1/1998 |
| GB | 2218831 | 11/1989 |
| GB | 2225637 | 6/1990 |
| JP | 54005785 | 1/1979 |
| JP | 54146633 | 11/1979 |
| JP | 62226278 | 10/1987 |
| JP | 5155024 | 6/1993 |
| JP | 5266002 | 10/1993 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9416774 | 8/1994 |
| WO | WO-95/09386 | 4/1995 |
| WO | WO-95/20199 | 7/1995 |
| WO | WO-9522131 | 8/1995 |
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97-08605 | 3/1997 |
| WO | WO-97/08605 | 3/1997 |
| WO | WO-97/12544 | 4/1997 |
| WO | WO-9737738 | 10/1997 |
| WO | WO-98/16895 | 4/1998 |

OTHER PUBLICATIONS

90009239_Request_for_Re-examination_6161095_2008_08_01.
+5V Powered Isolated RS-232 Drivers/Receivers Maxim Integrated Products.
Adilman; "Videogames: Knowing the Score"; Creative Computing; v9; p. 224(5); Dec. 1983; Dialog: File 148, Acc# 01891055.
AdOptimizer—Ad Management Software for Websites, Newsbytes, pNEW10040041, Oct. 4, 1996.
Albisser, A.M. "Intelligent Instrumentation in Diabetic Management", CRC Critical Reviews in Biomedical Engineering, vol. 17, No. 1, pp. 1-24.
Anonymous, "Health Hero Network, Inc. Receives First-Ever FDA Clearance for Connecting Medical Devices to Internet", PR Newswire, (Dec. 2, 1993), 3 pages.
Antique Collector, Putting the Lot on the Net, vol. 66, Issue 9, p. 26, Downloaded from Corporate Resource Net, Nov./Dec. 1995.
Bai, "Design of home healthcare network", IEEE 1997 pp. 1657-1658.
Billiard, A., et al. "Telematic Transmission of Computerized Blood Glucose Profiles for IDDm Patients", Diabetes Care, (Feb. 1991), vol. 14, No. 2, pp. 130-134.
Blood Glucose Monitors, Portable Health Device, (1998), vol. 17(9), pp. 253-271.
Bower, "Brain Clues to Energy-efficient Learning", Science News, (Apr. 1992), v. 141; p. 215(1); Dialog: File 647, Acct# 12123949.
Brenman et al.; Interaction of Nitric Oxide Synthase with the Postsynaptic Density Protein PSD-95 and α1-Syntrophin Mediated by PDZ Domaine; Cell; vol. 84, pp. 757-767, Mar. 8, 1996; Ref: XP-002104701.
Bruce, "Health Hero Network CEO, CNNfn", Digital Jam, (Dec. 1, 1999), 3.
Bruce, et al., "The Effects of Sympathetic Nervous System Activation and Psychological Stress . . . "; Diabetologia; 35(9); 1992; 835-843; Dialog: File 5, Acc#9629427. (9 pages).
Brunetti, P., et al., "A Simulation Study on a Self-Turning Portable Controller of Blood Glucose", The International Journal of Artificial Organs, (1993), vol. 16, No. 16, pp. 51-57.
Caprihan, A., et al., "A Simple Microcomputer for Biomedical Signal Processing", IECI '78 Annual Conference Proceedings on Industrial Applications of Microprocessors, (Mar. 20, 1978), 18-23.
Cathay Pacific Airways-USA receives more than 1,300 bids during first five days of CyberAuction; Business Wire, Oct. 18, 1995, p. 10181119.
Cathay Pacific Airways-USA to Hold First-Ever Internet CyberAuction; CyberTravelers Can Bid for 50 Business Class Round Trips to Hong Kong—No Minimum Bid; Business Wire; p. 9261084; Sep. 26, 1995; Dialog: File 148, Acc#08167091.
CD-ROM Mavericks: Proprietary TV-Based Players, Byte Guide to CD-ROM, pp. 100-105.
Central Fetal Monitoring Systems with Optical Disk Storage, New Technology Brief, (Nov./Dec. 1998), vol. 2, No. 6, pp. 249-251.
Cheng, Joe H., "PCT Search Report", (Jan. 11, 1996).
DigiPet Instruction Manual, 1997.
Digital Doggie; retrieved from URL http://www.virtualpet.com/vp/farm/gigapet/ddoggie.htm Apr. 23, 2000.
Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.
Edelson; "Fashion Reevaluates Flickering Fortunes of TV Home Shopping"; WWD; v170 n87; p. 1(3); Nov. 8, 1995; Dialog: File 148, Acc#08289119.
EP European Search Report, From 6858P005EP, (Mar. 27, 1998).
Fabietti, P.G., et al., "Wearable System for Acquisition, Processing and Storage of the Signal from Amperometric Glucose Sensors", The International Journal of Artificial Organs, (1991), vol. 14, No. 3, pp. 175-178.
Finston, "Parent + Teacher = Healthy Child", Diabetes Forecast, (Apr. 1994), v47 n9; p. 26(5); Dialog: file 149, Acc# 15804228.
Fox, "Not My Type: Type B Behavior, Type I Diabetes Plus Stress Equals Blood Sugar Blues", Health, (Mar. 1998), v20 n3; pp. 22(1); Dialog: File 149, Acc# 06397959.
Franklin; "Proposed Auction Rules for PCS: The FCC Plans to Use Competitive Bidding, but Exact Procedures are Undefined"; Cellular Business; v10 n13; p. 18(2); Dec. 1993; Dialog: File 148, Acc#06787310.
Frieberger, Paul, "Video Game Takes on Diabetes Superhero 'Captain Novolin' Offers Treatment Tips", San Francisco Examiner, (Jun. 26, 1992), Fourth Edition, Business Section B1.
Furnham, et al; "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.
Future of the Virtual Pet Industry, 1997 [retrieved on Apr. 23, 2000], Retrieved from <URL:www.virtualpet.com/vp/ future/future.htm>.
Gardner, et al.; "Comprehension and Appreciation of Humorous Material Following Brain Damage"; Brain; Sep. 1975; 98(3); pp. 399-412; Dialog: File 153, Acc#02859983. (14 pages).
Gauntlet (for PC) rulebook by Mindscape Inc. (Gauntlet by Apple);1985.
Giga Farm; retrieved from URL http://www.virtualpet.com/vp/farm/gigapet/gpfarm/gpfarm.htm Apr. 23, 2000.
Giga Pets, 1997 [retrieved on Apr. 23, 2000], Retrieved from <URL:www.virtualpet.com/vp/farm/gigapet/gigapet.htm>.
Gordon; "Auctions Become High Tech"; Dealer Business; v29 n7; p. 21(4); Mar. 1995; Dialog: File 148, Acc#07862519.
Guiffrida, et al., Should We Pay the Patient? Review of Financial Incentives to enhance Patient Compliance:, Biomedical Journal, (1997), vol. 315, pp. 703-707.
Hauben, Jay R., "A Brief History of the Cleveland Free-Net", available at http://www.ais.org/~irh/acn7-1.a09.html, (1995) pp. 1-4.

Hauser, et al., "Will Computers Replace or Complement the Diabetes Educators?", The Medical Journal of Australia, (Oct. 5, 1992), vol. 157, 489-491.

Horio, Hiroyuki, et al., "Clinical Telecommunication Network System for Home Monitoring", Medical & Biological Engineering & Computing, (Mar. 1994), vol. 32, 227-230.

How Flash Memory Works, Internet printout of URL address: http://www.howstuffworks.com/flash-memory4.htm, (Sep. 28, 2002), 2 pages.

Howey, et al., "A Rapidly Absorbed Analogue of Human Insulin"; Diabetes, vol. 43, Mar. 1994, pp. 396-402. (7 pages).

Hunter, "Technological Advances in Bedside Monitoring: Biosensors", Archives and Laboratory Medicine, (Jul. 1987), pp. 633-636.

Hutheesing, Nikhil, "An on-line gamble", Forbes, v157 n10 p. 288(1), May 20, 1996.

Introducing the Next Generation of About Your Diabetes, U.S. Pharmacopical Convention and American Diabetes Association, (1993).

Jaffrey et al.; "PIN: An Associated Protein Inhibitor of Neuronal Nitric Oxide Synthase"; Science; vol. 274; Nov. 1, 1996; Ref: XP 002050141.

Jimison et al., "Patient-Specific explanation in models of chronic disease", Revised Feb. 1992 Artificial Intelligence in Medicine 4 (1992) 191-205.

Jones, Chris, "Microsoft readies DocObject; technology will allow document editing in Web browsers", InfoWorld, v18 n18 p. 48(1), Apr. 29, 1996.

Kauffmann, et al., "Epidemiological Study of the Genetics and Environment of Asthma, Bronchial Hyperresponsiveness and Atropy", Am. J. Respir. Crit. Care Med., (1997), vol. 156, pp. S123-S129.

Kaufman, Steven, B., "The Learning Game", Nation's Business, (Nov. 1993).

Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.

Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.

Lachnit, Carroll, "Hawkin's Online Auction", Photo District News, vol. 16, Issue 1, p. 18, Jan. 1996.

Lacyk, John, "PCT Search Report", (Jun. 12, 1997).

Latman, N.S., "Evaluation of Electronic, Digital Blood Glucose Monitors", Biomedical Instrumentation and Technology, (1991), vol. 25, No. 1, 43-49.

Leyerle, Beverly J., et al., "The PDMS as a Focal Point for Distributed Patient Data", International Journal of Clinical Monitoring and Computing, (1988), vol. 5, pp. 155-161.

Luebke, Cathy, "Barrett-Jackson Auction Turns High-Tech", Business Journal, vol. 16, Issue 12, pp. 11, Jan. 19, 1996.

Makikawa, M., et al., "Microprocessor-Based Memory Device for Ambulatory Heart Rate and Physical Activity Recording", Methods of Information in Medicine, (1994), vol. 33, No. 1, pp. 94-96.

Marsh, David G. "Approaches Toward the Genetic Analysis of Complex Traits Asthma and Atrophy", Am. J. Respir.Crit.Care Med., (1997), vol. 156, pp. S-133-S138.

Martinez, Fernando D., "Complexities of the Genetics of Asthma", Am.J. Respir. Crit. Care Med., (1997), vol. 156, pp. S117-S122.

Marx, Wendy, "More than just the Scores: ESPNET SportsZone is a model for expanding brand names online", InformationWeek, n576 p. 61(2), Apr. 22, 1996.

Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.

McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.

Meissner, et al., "Building an Integrated Clinical and Research Network", Proceedings of the SPIE, (Oct. 24, 1995), vol. 2618, p. 92-99.

Miles, Laughton E., "A Portable Microcomputer for Long-Term Physiological Monitoring in the Home and Work Environment", Medical Monitoring in the Home and Work Environment, (1990), pp. 47-57.

Mims; "Psychological Testing"; Computers & Electronics; v23; p. 22(6); Feb. 1985; Dialog: File 47, Acc# 2654858.

Moore, "New Applications Break Through Storage Boundaries", Computer Technology Review, (Oct. 1999), vol. 19, No. 10 p. 1.

Mule. rulebook by Electronic Arts, 1983.

Nano Baby Instructions; retrieved from file://C:\My Documents\Nano Baby Instructions.htm Apr. 23, 2000.

Nano Fighter Pets; retrieved from URL http://www.virtualpet.com/vp/farm/nano/nfighter.htm Apr. 23, 2000.

Nano Page, 1997 [retrieved on Apr. 23, 2000], Retrieved from <URL:www.virtualpet.com/vp/farm/nano/nano.htm>.

Octhigotchi Instruction Manual, 1997. Dino-Kun Instruction Manual, 1997.

O'Donnell; "Alan's At It Again"; Bond Buyer; v309 n29448; p. 1(3); Jul. 21, 1994; Dialog: File 148, Acc#07478152.

Onsale Joins Fray as Online Shopping Picks Up Speed: Internet Booms; Computer Reseller News; Jun. 5, 1995; p. 73; Dialog: File 16, Acc#05649796.

Onsale Onsale Brings Thrill of Auctions and Bargain Hunting Online; Unique Internet retail service debuts with week-long charity auction for the Computer Museum in Boston, May 24, 1995; Dialog Abstract: File 610, Acc#0489267.

Pfeiffer, E. F., "The Glucose Sensor: The Missing Link in Diabetes Therapy", Hormone and Metabolic Research, (1990), vol. 24m Suppl. pp. 154-164.

Playmates Toys deals knockout blow to virtual pet competitors with introduction of Nano Fighter™ for Boys; New Nano Pet Fighting Pet Press Release; retrieved from URL http://www.virtualpet.com/vp/farm/nano/nfightpr.htm Apr. 23, 2000.

Playmates Toys leads Americas virtual pet craze into its next generation by introducting talking Nano Pals; Talking Nano Pet Press Release; Nov. 18, 1997; retrieved from URL http://www.virtualpet.com/vp/farm/nano/talkn/tnpress.htm on Apr. 23, 2000.

Poitout, V., et al. "A Glucose Monitoring System for on Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.

Polson, Gary "Recent Developments and Trends in Keychain Virtual Pets," 1997 [retrieved on Apr. 23, 2000], Retrieved from <URL:www.virtualpet.com/vp/future/trends1a.htm>.

Potter, David, "Fundamentals of PC-Based Data Acquisition", SENSORS, (Feb. 1994), pp. 12-20.

Reis, H, "Telemedicine: Transmitting Expertise to the Point of Care Toward an Electronic Patient Record"; '97, Nashville, TN, Apr. 27-May 3, 1997, pp. 248-256, v. 3.

Research project launched to improve health of America's communities; new Disney community in Florida is focus of program. Business Wire, p. 10011142. Oct. 1, 1996.

Results of the world's first on-line auction, http://www.christies.com. RO_AUCTION Auctioneers Property Database System and RO_AUCTION Auctioneers Accounting System; RO-AUCTION features; Dec. 4, 1995.

Roberts; "Diabetes and Stress: A Type A Connection?", Psychology Today, (Jul. 1987), v. 21; pp. 22(1); Dialog: File 149, Acc# 05038381.

Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.

Save the earth artrock auction, http://www.commerce.com.saveearth. Auction Web, http://www.ebay.com.

Schement, "An Intelligent Controller for Neurophysiological Experiments," Proceeding of the Annual Symposium on Computer Based Medical Systems, Durham, Jun. 14-17, 1992, p. 528, line 1—p. 529, line 21.

Schenkels, P., "Supplementary European Search Report", Application No. EP 97 92 2716, (Mar. 11, 2002).

Schork, Nicholas J., "Genetics of Complex Disease", Am.J.Respir. Crit. Care Me., (1997), vol. 156, pp. S103-S109.

Schrezenmeir, J. et al., "Computer Assisted Insulin Dosage Adjustment—Perspective for Diabetes Control", Hormone and Metabolic Research, Supplement Series, (1990), vol. 24, pp. 116-123.
Seigmann;"Nowhere to Go but Up"; PC Week; v12 n42, p. A5(1); Oct. 23, 1995; Dialog: File 148, Acc#08222496.
Seybold—New Horizons teams with Duke, Real Media; The Seybold Report on Desktop Publishing, v10 n12 p. 24(1), Aug. 12, 1996.
Shandle, Jack, "Who Will Dominate the Desktop in the 90's?", , Electronics, Feb. 1990, pp. 48-50. (3 pages) Cited by 2 patents.
Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.
Skolnick et al. "Simultaneous Analysis of Multiple Polymorphic Loci Using Amplified Sequence Polymorphisms (ASPs)"; Genomics. 2: 273-279.
Soeldner, J. S., "Treatment of Diabetes Mellitus by Devices", The American Journal of Medicine, (Jan. 1981), vol. 70, 183-194.
Spitzer et al.; "The moderating effect of age on self-care"; Western Journal of Nursing Research, v18, n2, p. 136(13), Apr. 1996.
Talking Nano Puppy; retrieved from URL http://www.virtualpet.com/vp/farm/nano/talkn/talkn.htm Apr. 23, 2000.
Tamagotchi, 1997 [retrieved on Apr. 23, 2000], Retrieved from <URL:www.virtualpet.com/vp/farm/lleg/lleg.htm>.
Tandy Radio Shack , "The description of the Tandy Radio Shack TRS-80 Model 100/102 device available at http://www.old-computuers.com/musuem/computer.asp?c=233", World Wide Web, (Feb. 13, 2004), 1-3.
Telemedicine Provides Two-Way Computer Link for Parents of Very Premature Infants. PR Newswire. p. 1007NEM034. Oct. 7, 1996.
Theme Hospital, product review 1996 [retrieved Apr. 21, 2000], Retrieved from <URL:www.vigilante.co.uk/ep/misc/hospital.htm>.
Towards a partnership of care, M2 Presswire, Jun. 14, 2000.
United Healthcare's OPTUM Division goes online to better health by announcing a unique internet application. PR Newswire, p. 0801MNTH004. Aug. 1, 1996.
Updike, Stuart J., et al., "Laboratory Evaluation of New Reusable Blood Glucose Sensor", Diabetes Care, (Nov./Dec. 1998), vol. 11, No. 10, pp. 801-807.
Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.
Vallera, D. A., et al., "Accuracy of Portable Blood Glucose Monitoring", American Journal of Clinical Pathology, (1991), vol. 95, No. 2, pp. 247-252.
Virtual Pet Product Reviews, 1997 [retrieved on Apr. 23, 2000], Retrieved from <URL:www.virtualpet.com/vp/farm/reviews/reviews,htm>.
Virtual Tomagutchi, 1998 [retrieved Apr. 23, 2000], Retrieved from <URL:www.sttf.org/english/action/tomagutchi.html>.
Voelker, Rebecca, "Shoe Leather Therapy is Gaining on TB", Jama, (Mar. 13, 1996), vol. 275, 743.
Wilkins, Aaron. "Expanding Internet access for health care consumers", Health Care Management Review, Summer, Jul. 1999, 24-30.
Wyatt, J. C., "Clinical Data Systems, Part 2: Components and Techniques", Lancet, (Dec. 1994), vol. 344, No. 8937, pp. 1609-1614.
Yoshizawa, Daisuke, et al., "The Development of a Data Processing System with Personal Computer MSX Standard System for Flow Injection Analysis", Journal of Flow Injection Analysis, (1988), V.5, No. 2, pp. 101-110.
Alere Medical Inc 's First Supplemental Response to Plaintiffs Amended Interrogatory No. 2. Jun. 20, 2008.
U.S. Appl. No. 90/010,053—Order Granting Request for Ex Parte Reexamination, Jan. 18, 2008.

* cited by examiner

TREATMENT REGIMEN COMPLIANCE AND EFFICACY WITH FEEDBACK

RELATED APPLICATIONS

This application is a continuation of application Ser. No. 10/233,296, filed Aug. 30, 2002, which is a continuation in-part of application Ser. No. 09/304,477, filed May 3, 1999, now abandoned. All of the above-identified applications are incorporated herein by reference in their entirety. This application is also a Continuation-in-Part of U.S. Ser. No. 09/237,194 filed on Jan. 26, 1999, which is a Continuation of Ser. No. 08/481,925, filed Jun. 7, 1995, now U.S. Pat. No. 5,899,855 issued on May 4, 1999, which is a Continuation of U.S. Ser. No. 08/233,397 filed on Apr. 26, 1994 now abandoned.

BACKGROUND OF THE INVENTION

1. Field of the Invention

This invention relates to interaction with a community of individuals, relating to treatment regimen compliance and efficacy, including supply and use of pharmaceuticals.

2. Related Art

When medical personnel prescribe treatment regimens for patients or "patients" undertake non-prescription treatment regimens (whether such regimens are prescribed or undertaken for medication, physical therapy, psychological therapy, self-improvement, or other purposes), a problem can arise in assuring that the patients comply with the requirements of the treatment regimen. For example, some patients are disorganized, forgetful, or simply unwilling to comply. When the treatment regimen has potential side effects, or when the treatment regimen is to be followed under stated conditions (for example: taking medicine with meals, not with alcohol, or in the evening), patient compliance can be relatively reduced even further. When the treatment regimen is relatively complex, some patients are even unable or unwilling to manage that treatment regimen.

Known methods for monitoring and controlling treatment regimens are relatively costly and limited in capability. Some known methods are described in the following patents:

U.S. Pat. No. 5,408,443, "Programmable Medication Dispensing System," issued Apr. 18, 1995 in the name of Edward D. Weinberger.

U.S. Pat. No. 5,642,731, "Method of and Apparatus for Monitoring the Management of Disease," issued Jul. 1, 1997 in the name of Bruce A. Kehr.

U.S. Pat. No. 5,752,235, "Electronic Medication Monitoring and Dispensing Method," issued May 12, 1998 in the name of Bruce A. Kehr, et al.

While these known methods generally achieve the goal of monitoring and controlling a treatment regimen, particularly a medication regimen, they suffer from several drawbacks and limitations.

First, there is a need to provide a portable system to monitor and encourage compliance, and facilitate data collection, so that patients are restricted as little as possible regarding their activities and movements.

Second, there is a need to determine if patients are actually complying with treatment regimens at times when the patients are relatively remote to client devices for the system. Known methods do not provide adequate feedback to determine whether patients are complying with the treatment regimen unless they remain relatively local to client devices.

Third, there is a need to determine whether treatment regimens have the desired and intended effects. Known methods do not provide adequate feedback to determine whether treatment regimens are effective, or whether patients are suffering any untoward side effects. Using known methods, medical personnel must generally wait for patients to complain, or for medical tests to show, that prescribed treatment regimens are inadequate or are producing side effects. Similarly, using known methods, patients undertaking non-prescribed treatment regimens generally do not have effective or convenient systems to monitor and record whether non-prescribed treatment regimens are producing intended results.

Fourth, there is a need to inform patients to follow treatment regimens, particularly when patients are forgetful or treatment regimens are complex. Although known methods do include reminders to patients, it would be advantageous to tailor those reminders to patients' actual compliance history (thus, providing fewer reminders when they are relatively less necessary and more reminders when they are relatively more necessary).

Fifth, there is a need to leverage expert knowledge to improve response to feedback from patients, and to reduce the time and expense required for medical personnel to individually monitor, evaluate and modify treatment regimens.

Sixth, there is a need to broaden application of reminder and expert knowledge leveraging systems beyond medication regimens, to include physical, psychological, self-improvement and other treatment regimens.

Accordingly, it would be advantageous to provide a portable device that can be coupled and uncoupled to a communication system with feedback to monitor patient compliance with, and effectiveness of, treatment regimens, so that input from patients regarding treatment regimens can be recorded, reviewed, analyzed and otherwise generally acted upon. Medical personnel and/or patients can thus (1) monitor compliance with treatment regimens, (2) monitor effectiveness or side effects of treatment regimens, (3) remind patients no more than necessary, and (4) possibly alter treatment regimens in response to feedback from patients. These advantages are achieved in embodiments of the invention in which a portable device is intermittently coupled to a client device in a client-server system, the patient enters information to the portable device about following the treatment regimen while the portable device is uncoupled, and medical personnel or the patient can receive that information and possibly alter the behavior of the portable device when the portable device is re-coupled to the system.

SUMMARY OF THE INVENTION

The invention provides a method and system for interaction with a community of individuals, relating to compliance with and effectiveness of treatment regimens, including supply and use of pharmaceuticals, using a protocol or other intelligent message which acts in place of a service provider and which is capable of collecting or imparting information to patients in place thereof. Individuals interact with the protocol or intelligent message to provide assistance in all aspects of treatment regimen compliance, data collection, supply or delivery, review and modification. These aspects can include (1) reminders regarding compliance with a selected treatment regimen for medication, physical therapy, psychological therapy, self-improvement, or some combination thereof, (2) data collection of facts regarding patient compliance, symptomology, possible drug interactions or side effects of medication if required by the treatment regimen, and other facts relevant to evaluation and possible modification of the treatment regimen; (3) networked integration with workstations for medical professionals to automate approvals and modifications, and refills and delivery of medication if required by the treatment regimen.

A system includes a set of client devices and a server device. A service provider determines a treatment regimen for selected patients, determines a protocol to be followed by the client devices to assist the patient in complying with that treatment regimen [in assisting with that medication regimen] and to maximize effectiveness of treatment, and sends that protocol to the server device. The server device can update (responsive to the protocol) selected instructions at the client devices, and can receive (responsive to selected instructions) information from the client devices regarding their associated patients.

In a first preferred embodiment, a client device, located locally to a patient, couples to a portable device (such as a cellular telephone, pager, "Palm Pilot" or other handheld computer, or watch), capable of being carried away by the patient to locations relatively remote from the client device. The client device can interact with the portable device: (1) to provide the portable device with the capability of reminding the patient regarding the treatment regimen, or (2) to provide the portable device with the capability of further data collection regarding the patient. The client device can interact with the portable device using a docking connection, an infrared connection, a radio-frequency connection, a plug-in connection, or another suitable connection.

DETAILED DESCRIPTION OF THE PREFERRED EMBODIMENT

In the following description, a preferred embodiment of the invention is described with regard to preferred process steps and data structures. Embodiments of the invention can be implemented using general purpose processors or special purpose processors operating under program control, or other circuits, adapted to particular process steps and data structures described herein. Implementation of the process steps and data structures described herein would not require undue experimentation or further invention.

System Elements

Figure 1:
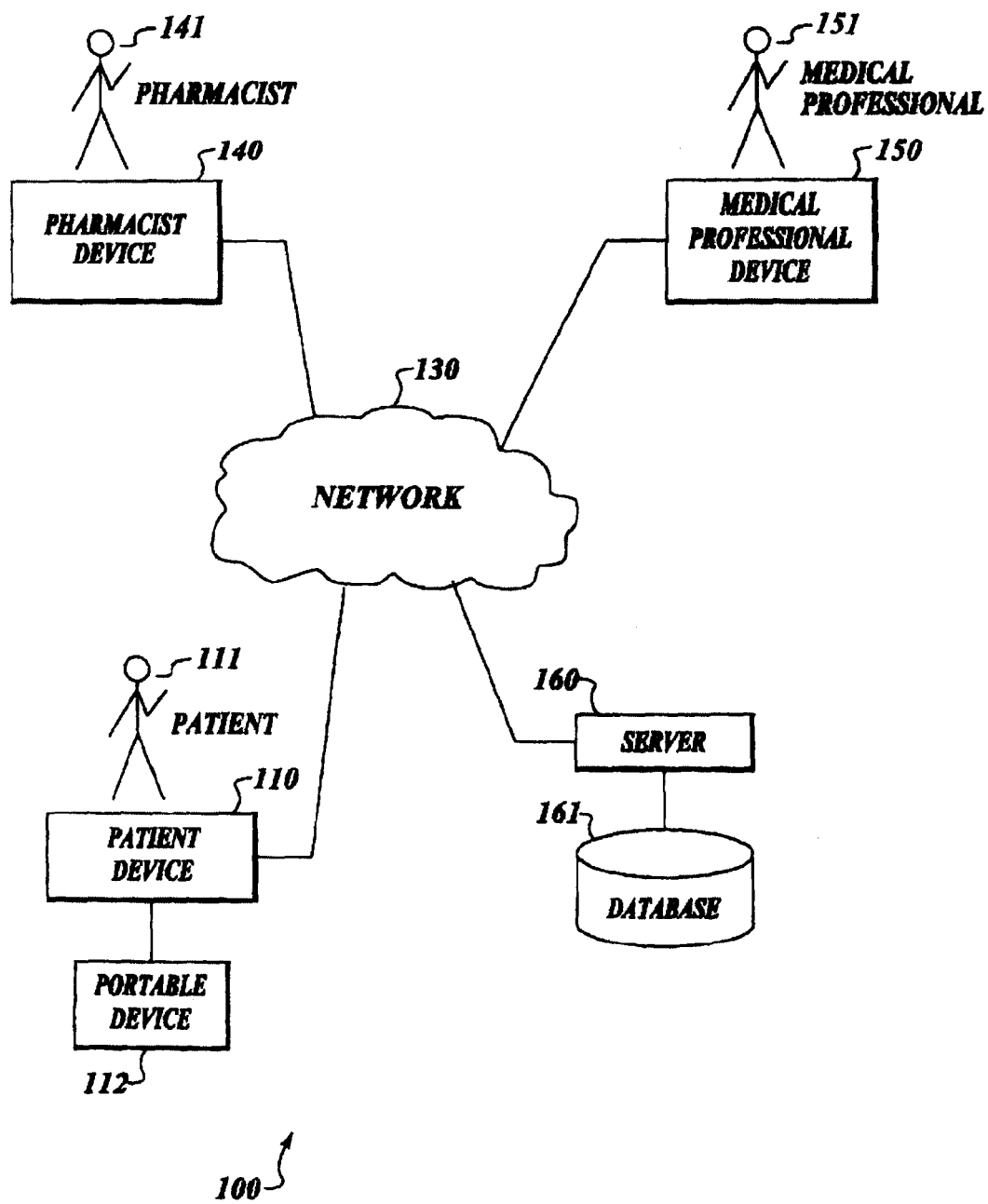
FIG. 1 shows a block diagram of a system for interaction with a community of individuals to encourage and monitor compliance with a treatment regimen, using a protocol or other intelligent message which acts in place of a service provider to collect and impart information relevant to the treatment regimen.

FIG. 1 shows a block diagram of a system 100 to encourage and monitor compliance with a treatment regimen using a protocol or other intelligent message which acts in place of a service provider to collect and impart information relevant to the treatment regimen, including a patient device 110, a pharmacist device 140, a medical professional device 150, and a server device 160, said devices being coupled using a communication network 130, and a portable device 112 which can be coupled to the patient device 110 to receive information regarding the treatment regimen and send feedback from the patient 111 responsive thereto.

For further information regarding a data structure and simplified patient interaction interface, and preferred embodiments of the patient device 110, pharmacist device 140, medical professional device 150, and the server device 160 including database 161 of treatment regimen information, see related application Ser. No. 09/201,323, filed Nov. 30, 1998, in the name of Stephen J. Brown, titled "Leveraging Interaction with A Community of Individuals," assigned to the same assignee, and other related applications incorporated by reference therein.

For further information regarding the protocol or other intelligent message used by the system, see related application Ser. No. 09/203,882, filed Dec. 1, 1998, in the name of Stephen J. Brown, titled "Remote User Data Collection Protocols Including Data Structures and User Interface," assigned to the same assignee, and other related applications incorporated by reference therein.

For further information regarding a medicine dispenser which can be used by the system, see related application Ser. No. 09/203,880, filed Dec. 1, 1998, in the name of Stephen J. Brown, et al., titled "Using A Computer Communication System With Feedback to Dispense Medicine," assigned to the same assignee, and other related applications incorporated by reference therein.

Portable Device

Figure 3:
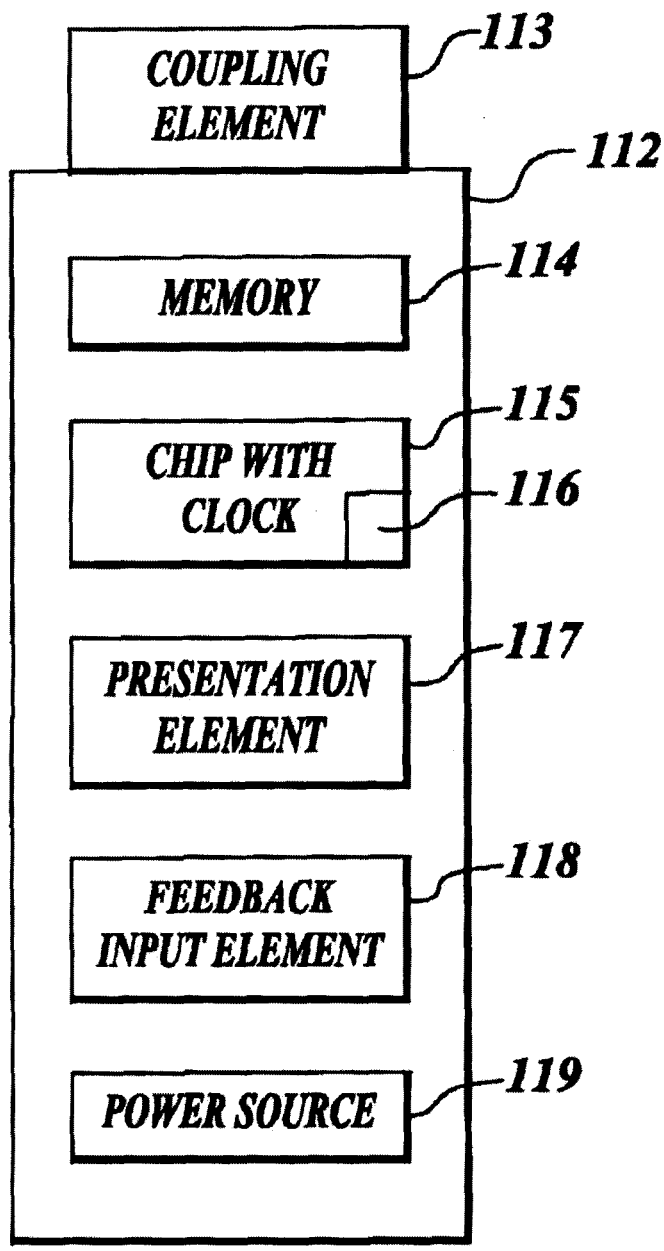
FIG. 3 shows a first preferred embodiment of a portable device used by the system to encourage and monitor compliance with a treatment regimen, and to collect and impart information relevant to the treatment regimen.

FIG. 3 shows a first preferred embodiment of a portable device 112 used by the system 100.

In a first preferred embodiment, the portable device 112 includes a coupling element 113 for coupling the portable device 112 to the patient device 110, a memory element 114, a processor chip 115 including a clock circuit 116, a presentation element 117, and a patient feedback input element 118.

A service provider determines a treatment regimen for selected patients 111 and a protocol to be followed by their portable devices 112 to assist the patients 111 in following the treatment regimen. The service provider sends the treatment regimen and protocol to the server device 160 where it is recorded in the database 161. The server device 160 sends the treatment regimen and protocol information to the patient device 110, and optionally to the pharmacist device 140 and the medical professional device 150.

The portable device 112 is coupled to the patient device 110 using the coupling element 113. The coupling element 113 may couple using a docking station, an infrared connection, a radio-frequency connection, a plug-in connection, other suitable means or any variant thereof While coupled, the treatment regimen and protocol information received by the patient device 110 is sent to the portable device 112 and recorded in the memory 114. In a first preferred embodiment, the power source 119 is rechargeable and the charge can be replenished by the patient device 110 while the portable device 112 is coupled to it. In alternative embodiments, the power source 119 is rechargeable and the charge can be replenished by some other device, or includes one or more disposable batteries.

After the treatment regimen and protocol information is recorded in the memory 114, the portable device 112 can be uncoupled from the patient device 110 and taken with the patient 110 to locations relatively or logically remote from the patient device 110. Whether the portable device 112 coupled or uncoupled to the patient device 110, when the patient 111 is due to perform an act according to the treatment regimen, the portable device 112 uses the presentation element 117 to provide a reminder message instructing the patient 111 to perform that act. In a first preferred embodiment, the act to be performed is related to compliance with a medication regimen including, without limitation, obtaining medicine, taking medicine, taking medicine with another substance such as food or water, not taking medicine with another substance such as alcohol or incompatible medications, or obtaining a prescription refill. In alternative embodiments, the act to be performed may be pursuant to a physical therapy regimen including, without limitation, exercising, stretching, changing position, or changing work routine; pursuant to a psychological therapy regimen including, without limitation, repeating an affirmation, meditation, self-hypnosis or other mental activity; or pursuant to a self-help regimen or other type of treatment regimen such as weight loss including, without limitation, drinking water or eating a snack.

The patient 111 performs the indicated act and enters a message into the portable device 112 confirming performance of the act using the patient feedback input element 118. Operation of the patient feedback input element 118 causes the processor chip 115 to cancel the reminder message, check the clock 116, and record the time and fact of performance in the memory 114. In a first preferred embodiment, the patient 111 also enters additional information relevant to monitoring and evaluating the treatment regimen in response to queries by the presentation element 117 in accordance with the treatment regimen and protocol.

The number of reminder messages provided to the patient 111, and the number of messages from the patient 111 confirming performance of the indicated acts and/or providing other information relevant to compliance with and effectiveness of the treatment regimen, is limited only by the memory capacity of the portable device 112.

In a first preferred embodiment, the presentation element 117 is a human-readable visual display using LCD's, LED's, or other suitable devices. In alternative preferred embodiments, the presentation element 117 can be a device which produces human-intelligible sound, or a combination of devices which produce human-intelligible visual and audible signals.

At some later time, the portable device 112 is re-coupled to the patient device 110 using the coupling element 113, causing the contents of the memory 114 to be downloaded into the patient device 110 and sent to the server device 160 for recording in the database 161. Such a time may be as is convenient to the patient 111, or according to a selected maximum time interval dictated by the treatment regimen and protocol, or as is required to replenish the power source 119 of the portable device 112, or in accordance with other requirements of the system 100.

At the server device 160, the protocol or other intelligent message reviews and compares the information provided by the patient 111 to the requirements of the treatment regimen in order to evaluate the effectiveness of the treatment regimen towards achieving treatment objectives and as to compliance of the patient 111 with the treatment regimen. The protocol may then leave the treatment regimen unchanged or modify it as needed to increase effectiveness and/or compliance; in either case, the server device 160 sends a message to the patient device 110 as to the regimen to be followed from that time forward. In a preferred embodiment, the server device 160 also sends that message to the pharmacist device 140 and the medical professional device 150. For additional information regarding the protocol used by the system 100 and interaction of the protocol with other elements of the system 100, see discussion above at System Elements regarding related applications.

In a first preferred embodiment, information regarding the entire course of the treatment regimen, such as each updated regimen and its effectiveness and relative compliance by the patient can be stored by each of those devices and displayed on demand. In alternative embodiments, only the server records the entire course, or only selected devices, or some combination thereof.

In a preferred embodiment, when a treatment regimen requires a patient 111 to take one or more medications, the portable device 112 can be coupled to a medication dispenser containing medication specified by the treatment regimen. In an alternative embodiment, the portable device 112 also controls the medication dispenser so as to release only the correct dosage of the correct medication at the correct time responsive to the treatment regimen. In a further alternative preferred embodiment, the dispenser automatically provides feedback to the portable device 112 when the correct medication is removed, canceling the reminder message and storing the feedback for subsequent downloading to the patient device 110 on the next occasion that the portable device 112 is coupled to the patient device 110.

The patient device 110 can be any device for electronic communication including, but not limited to, an application specific device, a hard-wired telephone, a cellular telephone, a pager, a personal desktop computer, a personal notebook computer, a hand-held computing device, an internet appliance, an internet-enabled television such as WebTV, personal digital assistant such as the Palm III, or any variant thereof.

The portable device 112 can be any portable device for electronic communication which is capable of being coupled to the patient device 110 including, without limitation, an application specific device, a cellular telephone, a pager, a personal notebook computer, a hand-held computing device, an internet appliance, a personal digital assistant such as the Palm III, a watch, or any variant thereof.

The feedback input element 118 can be any means of providing input to an electronic communication device including, but not limited to, a button, a telephone key, a computer keyboard key, a voice-response activator, or any variant or combination thereof.

Method of Operation

Figure 2:
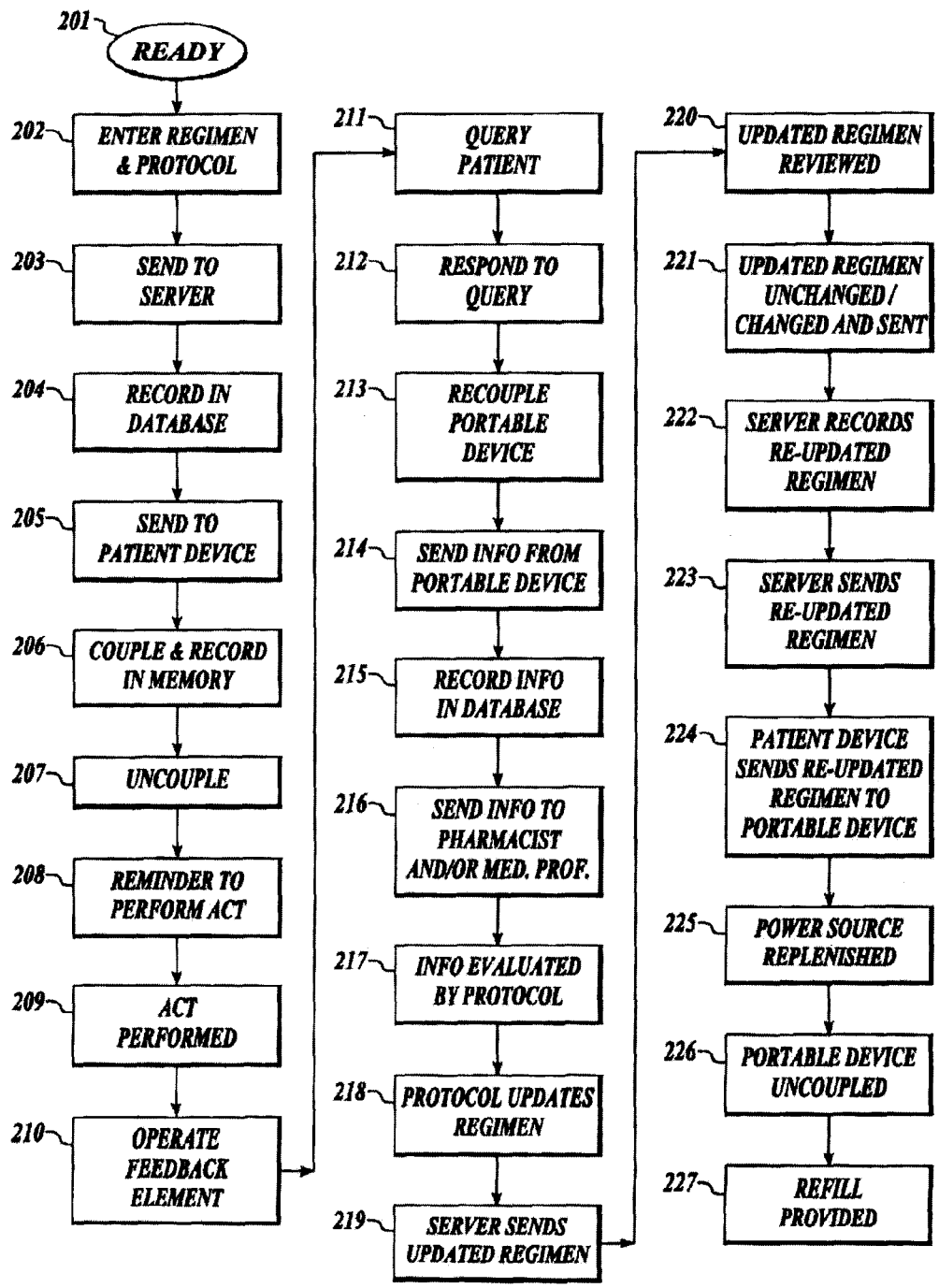
FIG. 2 shows a process flow diagram of a method for operating a system for interaction with a community of individuals to encourage and monitor compliance with a treatment regimen, using a protocol or other intelligent message which acts in place of a service provider to collect and impart information relevant to the treatment regimen.

FIG. 2 shows a process flow diagram of a method for operating a system for leveraging expert interaction with a community of individuals to encourage compliance with a treatment regimen and for collecting and imparting information relevant to that treatment regimen.

A method 200 is performed by the system 100, as follows:

At a flow point 201, the system 100 is ready to proceed.

At a step 202, a service provider enters information concerning a treatment regimen and protocol to be followed by the patient 111.

At a step 203, the treatment regimen and protocol information is sent to the server device 160 using the communications network 130.

At a step 204, the server device 160 records the treatment regimen and protocol information received from the service provider in the database 161.

At a step 205 in a preferred embodiment, the server device 160 sends the treatment regimen and protocol information to the patient device 110, the pharmacist device 140 and the medical professional device 150 using the communication network 130. In alternative embodiments, the server device 160 may send the treatment regimen and protocol information only to the patient device 110.

At a step 206, the portable device 112 is coupled to the patient device 110 and the treatment regimen and protocol information is copied into the memory 114 of the portable device 112.

At a step 207, the portable device 112 is uncoupled from the patient device 110 and is taken with the patient 111 to a location relatively remote from the patient device 110.

At a step 208, responsive to the treatment regimen and protocol information stored in the memory 114 in conjunction with input from the clock 116, the patient device 110 uses the presentation element 117 to provide a reminder message to the patient 111 that an act is required to be performed by the patient 111 and instructs the patient 111 regarding the act to be performed.

At a step 209, the patient 111 performs the indicated act as directed.

At a step 210, the patient 111 operates the feedback input element 118 on the portable device 112, canceling the reminder message.

At a step 211, the portable device 112 uses the presentation element 117 to query the patient 111 to provide information responsive to the protocol for evaluating the effectiveness of the treatment regimen.

At a step 212, the patient 111 operates the feedback input element 117 to provide information responsive to the queries, and that information is recorded in the memory 114.

At a step 213, the portable device 112 is re-coupled to the patient device 110.

At a step 214, the information stored in the memory 114 is sent to the patient device 110, which in turn sends that information to the server device 160 using the communication network 130.

At a step 215, the information received by the server device 160 is recorded in the database 161.

At a step 216, in a preferred embodiment the server device 160 sends the information received from the patient device 110 to the pharmacist device 140 and to the medical professional device 150 using the communication network 130. In an alternative embodiment, the server device 160 does not send the information received from the patient device 110 to the pharmacist device 140 or to the medical professional device 150, whether using the communication network 130 or otherwise.

At a step 217, the information received by the server device 160 from the patient device 110 is evaluated by the protocol.

At a step 218, the protocol updates the treatment regimen and either leaves it unchanged or modifies it in accordance with the protocol logic.

At a step 219 in a preferred embodiment, the server device 160 sends the updated treatment regimen information to the patient device 110, to the pharmacist device 140 and to the medical professional device 150, using the communication network 130. In an alternative embodiment, the server device 160 does not sent the updated treatment regimen information to the pharmacist device 140 or the medical professional device 150.

At a step 220 in a preferred embodiment, the pharmacist 141 and/or the medical professional 151 review and compare the original treatment regimen, the compliance and other information input by the patient 111, and the updated treatment regimen, and either leave the updated treatment regimen and protocol information unchanged or modify it as necessary. In an alternative embodiment, step 220 does not take place.

At a step 221 in a preferred embodiment, the treatment regimen and protocol information as unchanged or as modified by the pharmacist 141 and/or the medical professional 151 is sent to the server device 160 using the communication network 130. In an alternative embodiment, step 221 does not take place.

At a step 222, the server device 160 records the treatment regimen and protocol information as unchanged or as modified by the pharmacist 141 and/or the medical professional 151 in the database 161. In an alternative embodiment, step 222 does not take place.

At a step 223 in a preferred embodiment, the server device 160 sends the treatment regimen and protocol information as unchanged or as modified by the pharmacist 141 and/or the medical professional 151 to the patient device 110 using the communication network 130. In an alternative embodiment, step 223 does not take place.

At a step 224, the patient device 110 sends the updated treatment regimen information to the portable device 112 and it is recorded in the memory 114.

At a step 225, the patient device 110 replenishes the charge of the power source 119.

At a step 226, the patient 111 uncouples the portable device 112 from the patient device 110.

At a step 227, the pharmacist 141 provides a refill or new medicine to the patient 111 responsive to the treatment regimen and protocol information. In an alternative embodiment, step 227 does not take place.

Alternative Embodiments

Although preferred embodiments are disclosed herein, many variations are possible which remain within the concept, scope, and spirit of the invention, and these variations would become clear to those skilled in the art after perusal of this application.

The invention claimed is:

1. A portable device comprising:
   a signal interface configured to wirelessly communicate with a client device;
   a memory configured to store information about a treatment regimen, a program related to a protocol to be followed by the portable device, and an identification code associated with said program;
   an output user interface comprising a multi-line presentation element, said multi-line presentation element capable of displaying multiple lines of text and configured to display (i) said information regarding said treatment regimen and (ii) data received from a patient based on said information regarding said treatment regimen, wherein said information regarding said treatment regimen is displayed as alphanumeric messages of at least one line of text;
   an input user interface configured to receive said data from said patient; and
   a processor configured to record a time said data is received from said patient in said memory and send said data received from said patient along with said identification code to said client device.

2. The portable device of claim 1, wherein said information about a treatment regimen, said program related to said protocol, and said identification code associated with said program are received from said client device.

3. The portable device of claim 1, wherein said input user interface is further configured to notify said patient when to follow said treatment regimen.

4. The portable device of claim 1, wherein said input user interface is further configured to receive data that patient has followed said treatment regimen.

5. The portable device of claim 4, wherein said display comprises a liquid crystal display (LCD).

6. The portable device of claim 1, wherein said signal interface comprises a docking station and said client device comprises a personal desktop computer.

7. The portable device of claim 1, wherein said signal interface comprises an infrared connection and said portable device further comprises a personal digital assistant.

8. The portable device of claim 1, wherein said signal interface comprises a radio-frequency connection and said portable device further comprises a cellular telephone.

9. The portable device of claim 1, wherein said signal interface comprises a plug-in connection and said client device comprises a hard-wired phone.

10. The portable device of claim 1, wherein said portable device comprises a hand-held computing device.

11. The portable device of claim 1, wherein said portable device comprises an application specific device.

12. The portable device of claim 1, wherein said portable device comprises a pager.

13. The portable device of claim 1, wherein said portable device comprises a personal notebook computer.

14. The portable device of claim 1, wherein said portable device comprises an Internet appliance.

15. The portable device of claim 1, wherein said client device comprises an Internet-enabled television.

16. The portable device according to claim 1, wherein said memory comprises a Flash memory.

17. A system comprising:
a portable device configured to receive a first information about a treatment regimen and send a second information about compliance with said treatment regimen, wherein said portable device comprises (a) a memory configured to store said first information regarding said treatment regimen, a program related to a protocol to be followed by the portable device, and identification data associated with the program and (b) a multi-line presentation element, said multi-line presentation element capable of displaying multiple lines of text and configured to display (i) said first information regarding said treatment regimen and (ii) said second information, wherein said first information is displayed as alphanumeric messages of at least one line of text and said second information comprises data received from a patient based on said first information; and
a client device configured to (i) receive said second information and said identification data associated with said program from said portable device and (ii) send said second information and said identification data associated with said program to a server, wherein said server compares said first information with said second information.

18. The system according to claim 17, wherein said client device receives said second information and said identification data associated with said program from said memory of said portable device.

19. A method comprising the steps of:
(A) receiving a first information about a treatment regimen by a portable device and inputting a second information about compliance with said treatment regimen into said portable device, wherein said portable device comprises (a) a memory configured to store said first information regarding said treatment regimen, a program related to a protocol to be followed by said portable device, and an identification code associated with said program and (b) a multi-line display, said multi-line display is capable of displaying multiple lines of text and configured to present (i) said first information regarding said treatment regimen and (ii) said second information regarding compliance with said treatment regimen, and said first information is displayed as one or more alphanumeric messages of at least one line of text, and wherein said second information comprises data received from a patient based on said first information; and
(B) receiving said second information and said identification code associated with said program by a client device from said portable device and sending said second information and said identification code associated with said program to a server.

20. The method according to claim 19, wherein step (B) further comprises comparing said first information with said second information by said server.

* * * * *